United States Patent [19]

Mussi

[11] Patent Number: 5,665,596
[45] Date of Patent: Sep. 9, 1997

[54] DEVICE FOR CELL CO-CULTURE AND METHOD FOR ITS USE IN CULTURING CELLS

[75] Inventor: Edward F. Mussi, Saline, Mich.

[73] Assignee: Becton, Dickinson and Company, Franklin Lakes, N.J.

[21] Appl. No.: 509,394

[22] Filed: Jul. 31, 1995

[51] Int. Cl.$^6$ .................................................. C12M 3/00
[52] U.S. Cl. ................... 435/373; 435/305.4; 435/305.1; 435/401
[58] Field of Search ................ 435/287.1, 305.1, 435/305.4, 240.241

[56] References Cited

U.S. PATENT DOCUMENTS

| | | | |
|---|---|---|---|
| 3,245,759 | 4/1966 | Eweson | 23/259.1 |
| 4,871,674 | 10/1989 | Matsui et al. | 435/284 |
| 5,026,649 | 6/1991 | Lyman et al. | 435/284 |
| 5,409,829 | 4/1995 | Mussi et al. | 435/240.241 |

FOREIGN PATENT DOCUMENTS

| | | |
|---|---|---|
| 613004 | 1/1961 | Canada. |
| 1592743 | 6/1965 | Germany. |
| 0524908A2 | 7/1992 | Switzerland. |

OTHER PUBLICATIONS

Magnum et al., *In Vitro Cell Dev. Biol.* 26:1135–1143 (Dec. 1990), "Co–Culture of Primary Pulmonary Cells to Model Alveolar Injury and Translocation of Protein".

Madara et al., *J. Tissue Cult. Method.* 14:209–216, (1992), "A Simple Approach to Electrical Parameters of Cultured Epithelial Monolayers: Use In Assessing Neturophil–Epithelial Interactions".

Miller et al., *J. Tissue Cult. Method,* 14:217–224, "Application of Cultured Endothelial Cells of the Brain Microvasculature in the Study of the Blood–Brain Barrier".

*Science,* 266:564–565 (1995), "Finding Clues About How Embryo Structures Form".

*Primary Examiner*—David A. Redding
*Attorney, Agent, or Firm*—Arthur D. Dawson

[57] ABSTRACT

A two piece co-culture device having receptacles for containing fluid on two sides of a porous membrane includes an insert with a passageway therethrough with a longitudinal axis. The insert has a first end, a second end and a sidewall, the second end has an outside diameter and a porous membrane with a first side and a second side bonded thereover substantially perpendicular to the axis. The membrane closes the second end of the insert forming a a first receptacle for containing fluid on the first side of the porous membrane within the insert that is open to the first end. The first end has a flange extending outwardly from at least a portion of the sidewall substantially perpendicular to the axis for suspending the insert in a well. The device also includes an adapter for forming a second receptacle for containing fluid on the second side of the porous membrane. The adapter has an open end, an insert end and a passage with a longitudinal axis extending therethrough. The passage through the adapter has an inside diameter at the insert end sized to accept the outside diameter of the second end of the insert when the insert end of the adapter is coaxially releasably mounted on the second end of said insert. The second end of the insert is fit within the adapter to close the passage and form the second receptacle on the second side of the porous membrane that is open toward the open end of the adapter.

18 Claims, 4 Drawing Sheets

DEVICE FOR CELL CO-CULTURE AND METHOD FOR ITS USE IN CULTURING CELLS

FIELD OF INVENTION

The present invention generally relates to the co-culture of cells and more particularly to an adapter and device useful for establishing populations of cells on both sides of a porous membrane.

BACKGROUND

Culturing of cells of various types has become a routine process in many laboratories. Cells are cultured to harvest compounds, to test for various sensitivities to potentially toxic compounds and even to provide tissue for grafts. This work generally is a monoculture, i.e., cells of one type are grown in a suitable medium.

More recently, interest has developed in the co-culture of cells. Co-culture of cells involves growing one population of cells in the presence of another population of cells. Co-culture of cells is important for study of inflammation reactions, cell differentiation processes and blood brain permeability studies.

Representative literature reports related to cell co-culture include: Magnum et at., *In Vitro. Cell Dev. Biol.* 26:1135–1143 (December 1990), "Co-Culture of Primary Pulmonary Cells to Model Alveolar Injury and Translocation of Protein"; Madara et at., *J. Tissue Cult. Method*, 14:209–216, (1992), "A Simple Approach to Electrical Parameters of Cultured Epithelial Monolayers: Use in Assessing Neutrophil-Epithelial Interactions"; Miller et al., *J. Tissue Cult. Method*, 14:217–224, "Application of Cultured Endothelial Cells of the Brain Microvasculature in the Study of the Blood-Brain Barrier; and *Science*, 266:564–565 (1995), "Finding Clues About How Embryo Structures Form." The above referenced articles are cited to provide background regarding the in vitro study of interaction between one cell type and another.

Miller et at., cited above, describes culturing of cells on solid plastic surfaces and filters or membrane inserts. Miller et at. reports that bovine brain endothelial cells (BBEC) cultured on filters or membrane inserts provide an advantage over BBEC cultured on solid plastic surfaces. This advantage is that cell polarity with respect to metabolism or receptor distribution can be examined. Miller et al. further states that BBEC culture on filters or membrane inserts is required for determining the trans cellular transport or permeability of a compound across the cellular monolayer.

The above referenced *Science* article describes studies on kidney structure development. The article reports Mesenchymal cells co-cultured with cells producing Wnt-1 protein differentiate into kidney structures, including nephron tubular and glomular tissue and reports that this effect is not seen with control cells.

In response to the developing need for devices and equipment to co-culture cells, a co-culture system is disclosed in the commonly assigned U.S. application Ser. No. to Mussi et at. 08/124,415. The disclosure provides a complete self-contained system for preparing a co-culture of cells.

U.S. Pat. No. 5,026,649 to Lyman et at. discloses an insert device that can be utilized to culture and co-culture cells.

U.S. Pat. No. 4,871,674 to Matsui et al. discloses an insert for culturing cells having a porous membrane forming the bottom of a cylinder. The cylinder additionally has provisions for being suspended in a well.

Both the Lyman et at. disclosure and the Matsui et al. disclosure can be used to culture cells on a membrane, but neither is well suited for growing populations of cells on opposite sides of a membrane. The cell culture system disclosed in Ser. No. 08/124,415 is well suited to culture cells on both sides of a membrane, but requires a series of manipulations that may be time consuming for screening studies where multiple co-cultures are being developed.

In view of the increasing interest in co-culture of cells, there is a need for a simple to use apparatus for co-culture of cells that enables the practitioner to rapidly develop co-cultures on both sides of a porous membrane of a cell culture insert. Such a device and a method for it use is described below.

SUMMARY

A two piece co-culture device of the present invention has fluid containing open receptacles on both sides of a porous membrane. The device includes a cell culture insert with an axial passageway therethrough. The cell culture insert has a first end, a second end and a sidewall. The porous membrane is bonded to the second end of the insert substantially perpendicular to the axial passageway. The membrane closes the second end of the insert to form a first receptacle on a first side of the membrane within the insert that is open to the first end. The device further includes a releasably mounted adapter on the second end of the insert. The adapter forms a fluid containing second receptacle on a second side of the porous membrane. The adapter has a first end, a second end and a passage with a longitudinal axis extending through the adapter from the open end to the insert end. The passage has an inside diameter at the insert end sized to accept an outside diameter of the cell culture insert second end. When the adapter is coaxially releasably mounted on the second end of the insert, the cell culture insert second end fits within the adapter insert end, closing the adapter passage and forming the second receptacle over the second side of the porous membrane that is open toward the open end of the adapter.

An adapter of the present invention that is useful to form a second receptacle for containing fluid on an exterior side of a porous membrane of a cell culture insert with a first receptacle has an insert end, an open end and a passage with a longitudinal axis therethrough. The insert end of the adapter has an inside diameter sized to accept an end of the cell culture insert with the porous membrane mounted thereon. When the adapter is releasably coaxially mounted over the end of the cell culture insert, the insert closes the passage in the adapter to form the second receptacle over the exterior side of the porous membrane on the cell culture insert that is open toward the open end of the adapter.

A method for forming a second receptacle for containing fluid on an exterior side of a porous membrane of a cell culture insert with a first receptacle therewithin includes placing an adapter with an insert end, an open end and a passage therethrough with a longitudinal axis over an end of the cell culture insert with the porous membrane mounted thereon. The insert end of the adapter has an inside diameter sized to accept the end of the cell culture insert with the membrane. The end of the insert closes the adapter passage forming the fluid containing second receptacle over the exterior side of the membrane within the adapter open to the open of the adapter.

The adapter, device and method of the present invention provide the practitioner of cell culture with a simple-to-use reliable apparatus useful for culturing cells on both sides of a porous membrane and a method for forming a receptacle on the exterior side of a cell culture insert membrane.

DETAILED DESCRIPTION

Figure 1:
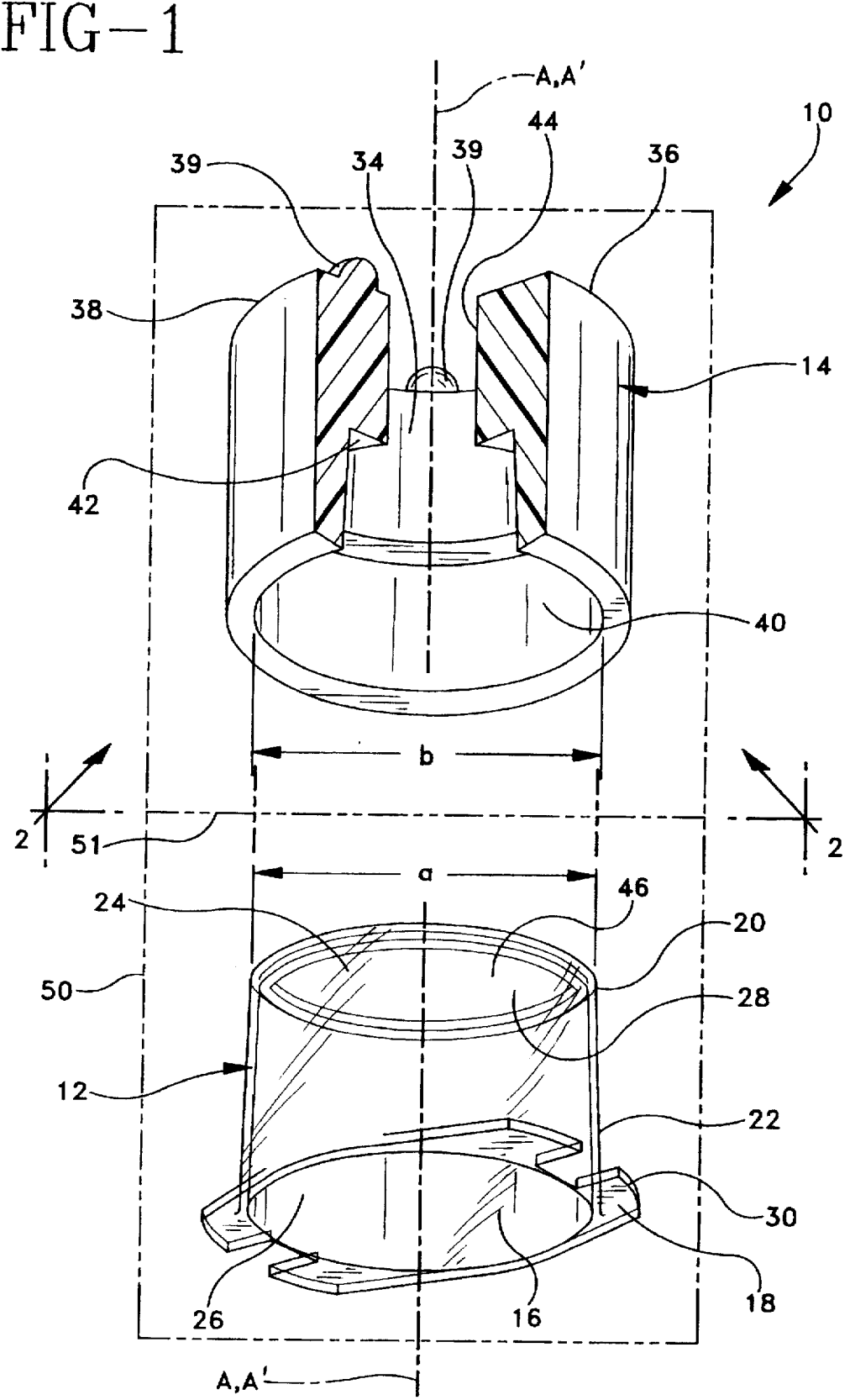
FIG. 1 is partial cut-away exploded perspective view of a two-piece co-culture device of the present invention.

While this invention is satisfied by embodiments in many different forms, there is shown in the drawings and is herein described, several embodiments of the invention with the understanding that the present disclosure is to be considered descriptive of the principles of the present invention and is not intended to limit the scope of the invention to the embodiments illustrated. The scope of the invention is measured by the appended claims and their equivalents.

Figure 2:
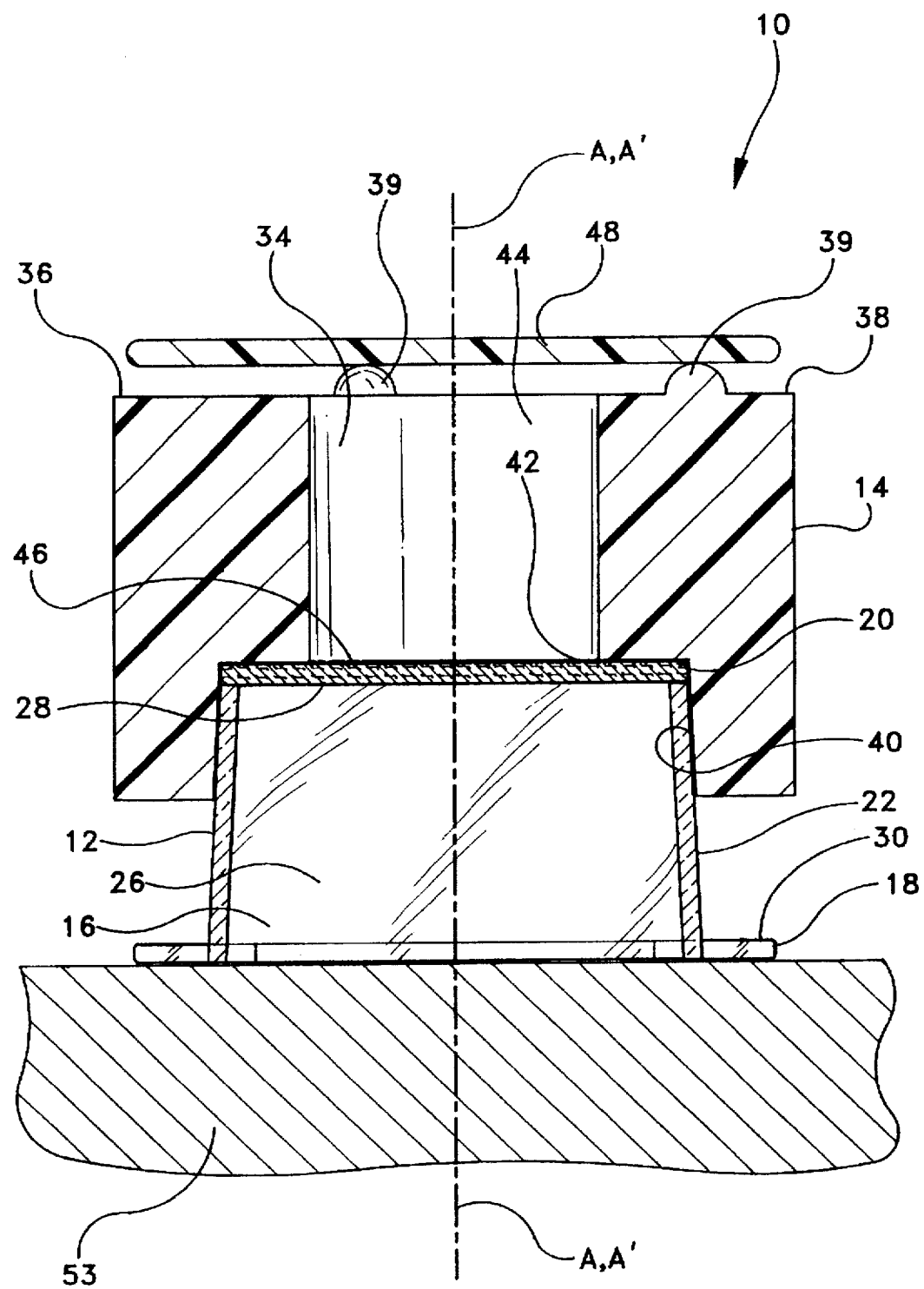
FIG. 2 is a cross-sectional view of the assembled device of FIG. 1 along the line 2—2 shown standing on a surface.

Referring to FIGS. 1 and 2, a two-piece co-culture device of the present invention 10 includes a cell culture insert 12 and an adapter 14. Cell culture insert 12 has a passageway 16 having a longitudinal axis "A" therethrough. Insert 12 has a first end 18, a second end 20 and a sidewall 22. Second end 20 has an outside diameter "a" and has a porous membrane 24 bonded onto it substantially perpendicularly to axis "A." Porous membrane 24 closes passageway 16 at second end 20 to form a first receptacle 26 on a first side 28 of porous membrane 24. First receptacle 26 is open toward first end 18 of the cell culture insert. Preferably, first end 18 further includes a flange 30 extending outwardly substantially perpendicularly to axis "A" from a least a portion of sidewall 22. Flange 30 is useful for suspending the insert in a well.

Preferred device 10 includes an adapter 14. Adapter 14 has a passage 34 with a longitudinal axis "A'." The preferred adapter has an open end 36 with a surface 38, preferably having a plurality of spacers 39 thereon, and an insert end 40. Passage 34 has an inside diameter "b" at insert end 40 and preferably has a shoulder 42 intermediate open end 36 and insert end 40. Diameter "b" at insert end 40 is sized to accept outside diameter "a" of second end 20 of insert 12. When insert end 40 is coaxially releasably mounted on second end 20 of the insert, second end 20 fits within adapter 14 and contacts preferred shoulder 42 to close passage 34 and form a second receptacle 44 with a second side 46 of the membrane. Receptacle 44 is open toward open end 36 of the adapter. Device 10 may also include a lid 48 as shown schematically in FIG. 2.

Preferred adapter 32 may also be supplied separately for use with a variety of inserts. When the adapter is supplied separately, inside diameter "b" of insert end 40 preferably is made available in a variety of dimensions to accept the membrane end of common commercially available inserts. Adapter 32 may be formed from a variety of materials including, but not limited to, thermoplastics, thermoset resins, cast resins or may be machined from metals such as stainless steel. Preferably, adapter 32 is formed from a thermoplastic elastomer. Suitable thermoplastic elastomers include, but are not limited to, silicone rubber, styrene-ethylene-butylene-styrene block copolymer with dispersed polysiloxane, polyurethane rubber, polypropylene alloys and the like. C-Flex, a styrene-ethylene-butylene-styrene block copolymer with dispersed polysiloxane, available from Consolidated Polymer Technologies, Clearwater, FL, is a preferred thermoplastic elastomer. The thermoplastic elastomer selected is resilient, with a durometer between about 30 to about 70 Shore A. Preferably, the durometer of the elastomer used for the adapter is about 50 Shore A. Any thermoplastic elastomer selected preferably is substantially free from materials that are extractable into cell culture media thereby substantially avoiding introduction of contaminants into the cell culture environment.

Preferably, device 10 is sealed in a package 50, shown in phantom in FIG. 1, formed from materials substantially resistant to the passage of microorganisms. The packaged device then preferably is exposed to conditions capable of rendering any microorganisms therein nonviable. Suitable conditions for rendering microorganisms nonviable include, but are not limited to, ethylene oxide gas exposure or exposure to ionizing radiation. When preferred adapter 32 is supplied as a separate item, it is preferably sealed in a package 51, also shown in phantom in FIG. 1. The package and treatment of the packaged adapter is substantially similar to the packaging and exposure described for preferred device 10.

Cell culture insert 12 may be formed from thermoplastic materials such as polycarbonate, polyethylene terephthalate, polyester, styrene-acrylonitrile and the like. Membrane 16 may be formed from materials such as polyethylene terephthalate, polycarbonate and the like. The membrane preferably has a thickness between about 20 microns to about 30 microns with open pores therethrough between about 0.2 microns to about 10 microns in diameter. Preferably, the membrane has a pore density between about $0.1 \times 10^6$ to about $10.0 \times 10^6$ pores per square centimeter. Preferred materials for the microporous membrane are available from "Cyclopore" (Avenue Einstein, Louvain-la-Neuve, Belgium) and "Poretics" (Livermore, Calif.). Membrane 24 may be bonded to insert 12 by any suitable bonding technique known to provide a secure attachment between the insert and the membrane including, but not limited to, adhesive bonding, solvent bonding, heat sealing and ultrasonic welding. Preferably, insert 12 is substantially transparent and is formed by injection molding from polyethyleneterethalate. Preferably, porous membrane 24 is bonded to insert 12 by solvent bonding.

Referring to FIGS. 1 and 2, a preferred method for forming second receptacle 44 includes placing adapter 14 over second end 20 of the cell culture insert. Preferably, cell culture insert end 20 then contacts shoulder 42 to close passage 34 forming a substantially liquid tight fluid containing second receptacle 44 over exterior side 46 of membrane 24 within adapter 32 that is open to end 36 of the adapter.

Figure 3:
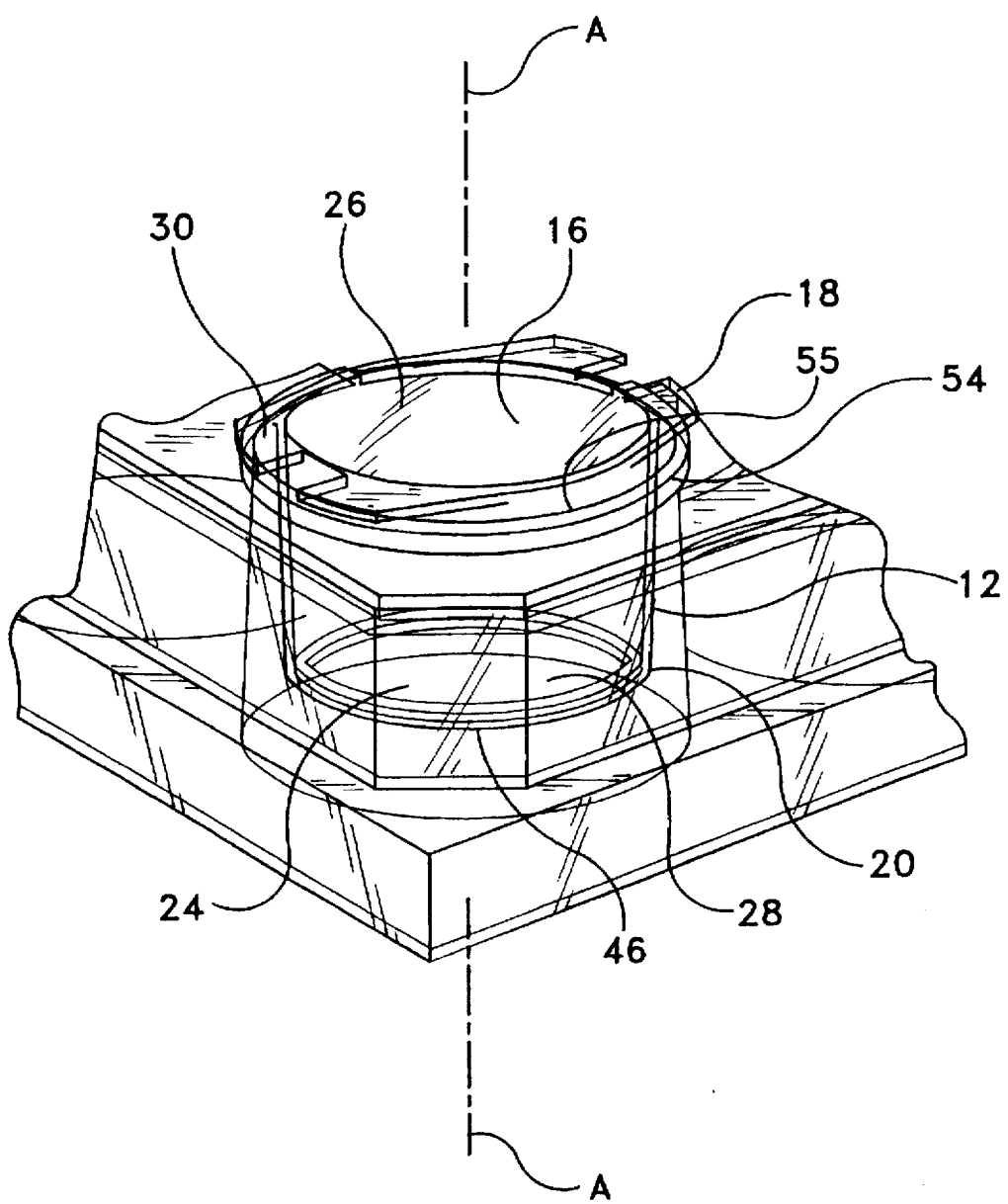
FIG. 3 is a perspective view of the insert component of the co-culture device of FIG. 1 suspended in a well.

A preferred method for culturing one population of cells on first side 28 of porous membrane 24 and another population of cells on second side 46 of porous membrane 24 of cell culture insert 12 includes placing device 10 on a surface 53, as shown in FIG. 2, so that second receptacle 44 is upward and open. In the case where adapter 14 is supplied separately, the method of forming second receptacle 44 described above includes selecting adapter 14 with the appropriate inside diameter "b" to accept the outside diameter "a" of the insert being used and then mounting the adapter to form second receptacle 44. The preferred method then includes adding a suspension of a first population of cells in a suitable medium into second receptacle 44 and incubating the device with the cell suspension therein so that the first population of cells forms a substantially confluent layer on second side 46 of the membrane. During the incubation, the operator may choose to place lid 48 over receptacle 44 to substantially prevent contamination of the contents of the receptacle. When lid 48 or any other similar cover is used, preferred spacers 39 support the lid above surface 38 of open end 36. After the incubation, the preferred method includes removing the medium from second receptacle 44 and removing adapter 14 from insert 12. Referring to FIG. 3, the preferred method then includes suspending insert 12 in a container 54 having a well 55 so that second end 20 is within well 55 using flange 30. Preferably, when the insert is suspended in the well first receptacle 26 opens upwardly. When following the preferred method, the operator then adds a suspension of a second population of cells in a suitable medium into first receptacle 26, places a sufficient quantity of a suitable medium into well 55 and incubates the container with the insert. For particular applications, the preferred sequence described above may be modified. The modification may include omitting steps, adding steps or by following the steps in a different order. The preferred method is not intended to be limitive of the present invention, but rather to be descriptive.

Figure 4:
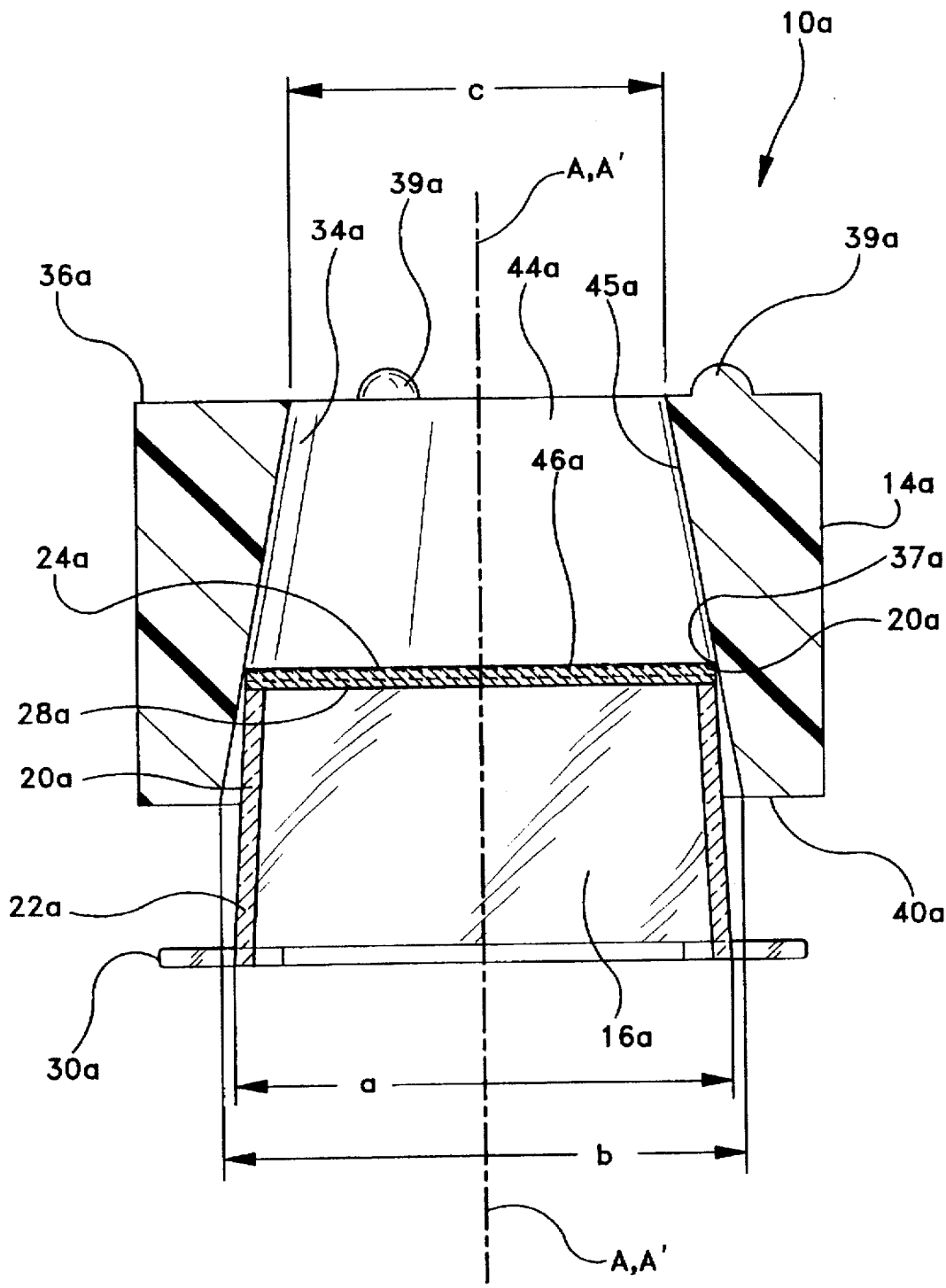
FIG. 4 illustrates another embodiment of the assembled device of FIG. 1 in a view analogous to the view of FIG. 2.

Referring to FIG. 4, another embodiment of the adapter of the present invention is illustrated as mounted on a cell culture insert. In this embodiment the structure of the device is Substantially similar to the device of FIGS. 1 and 2. Accordingly, substantially similar components that perform substantially similar functions are numbered identically to those components of the embodiment of FIGS. 1-2 except that a suffix "a" is used to identify those components in FIG. 4. In this embodiment, a two-piece co-culture device of the present invention 10a has a first receptacle 26a and a second receptacle 44a for containing fluid on a first side 28a and a second side 46a, respectively, of a porous membrane 24a. Device 10a includes an adapter 32a to form second receptacle 44a for containing fluid on second side 46a of porous membrane 24a. Adapter 14a has a passage 34a with a longitudinal axis "A'." The adapter has an open end 36a and an insert end 40a. In this embodiment, open end 36a has a diameter "c" that is smaller than diameter "b" at insert end 40a so that passage 34a forms a taper 45 between open end 36a and insert end 40a. This taper effectively serves the same role as shoulder 42 in the previously described embodiments of FIGS. 1 and 2. When insert end 40a is coaxially releasably mounted on second end 20a of the insert, second end 20a fits within adapter 14a to close passage 34a and to form second receptacle 44a at an interference fit 37 with second side 46a of the membrane. Receptacle 44a is open toward open end 36a of the adapter.

The device and adapter of the present invention provide practitioners of cell culture with a simple ready-to-use apparatus for growing populations of cells on both sides of a porous membrane. The method of forming the second receptacle on the exterior side of a porous membrane of a cell culture insert is simpler than the methods reported in the literature of adhesively bonding a ring onto the insert. Additionally, the method of the present invention is much less technique sensitive and less likely to introduce contaminants into the cell culture environment than the reported methods.

What is claimed is:

1. A two piece co-culture device having receptacles for containing fluid on two sides of a porous membrane consisting essentially of:

an insert having a passageway therethrough with a longitudinal axis, said insert having a first end, a second end and a sidewall, said second end having an outside diameter and a porous membrane having a first side and a second side bonded thereover substantially perpendicular to said axis, said membrane closing said passageway at said second end forming a first receptacle for containing fluid on said first side of said porous membrane within said insert open to said first end; and an adapter, for forming a second receptacle for containing fluid on said second side of said porous membrane, said adapter having an open end, an insert end and a passage with a longitudinal axis extending therethrough, said passage having an inside diameter at said insert end, said insert end inside diameter being sized to accept said outside diameter of second end of said insert, said insert end of said adapter being coaxially releasably mounted on said second end of said insert, said second end of said insert being fit within said adapter to close said passage and to form said second receptacle on said second side of said porous membrane open toward said open end of said adapter.

2. The device of claim 1 wherein said adapter further comprises a shoulder in said passage intermediate said insert end and said open end so that when the second end of said insert is releasably fit with said adapter, said second end is substantially in contact with said shoulder to close said passage.

3. The device of claim 1 wherein said adapter further comprises an inside diameter at said open end being smaller than said inside diameter at said insert end and said outside diameter of said second end of said insert so that said passage forms a taper from said insert end to said open end thereby forming an interference fit with said second end of said insert to close said passage and to form said second receptacle when said insert is fit within said adapter.

4. A packaged co-culture device comprising the device of claim 1 contained in a package formed from material substantially resistant to the passage of microorganisms.

5. The device of claim 1 further comprising said first end having a flange extending outwardly from at least a portion of said sidewall substantially perpendicular to said axis for suspending said insert in a well.

6. The device of claim 1 wherein said insert is formed from a material selected from the group consisting of polycarbonate, polyethylene terephthalate, polyester and styrene-acrylonitrile.

7. The device of claim 1 wherein said membrane is formed from a material selected from the group consisting of polyethylene terephthalate and polycarbonate, said membrane having a thickness between about 20 microns to about 30 microns and having open pores therethrough between about 0.2 microns to about 10 microns in diameter, said membrane having a pore density between about $0.1 \times 10^6$ to about $10.0 \times 10^6$ pores per square centimeter.

8. The device of claim 1 wherein said membrane is bonded to said insert by a method selected from the group consisting of adhesive bonding, solvent bonding, heat sealing and ultrasonic welding.

9. The device of claim 1 wherein said adapter is formed from a thermoplastic elastomer.

10. The device of claim 1 further comprising a lid for covering said second receptacle.

11. An adapter for forming a receptacle for containing fluid on an exterior side of a porous membrane of a cell culture insert consisting essentially of an insert end, an open end and a passage with a longitudinal axis therethrough, said insert end having an inside diameter sized to accept an end having an outside diameter of the cell culture insert having the porous membrane mounted thereon, the membrane having an interior side and an exterior side, so that when said adapter is releasably coaxially mounted over the end of the cell culture insert, the insert closes said passage to form a receptacle on the exterior side of the porous membrane toward slid open end of said adapter.

12. The adapter of claim 11 further comprising an inside diameter at said open end being smaller that said inside diameter at said insert end and the outside diameter of the second end of the insert so that, said passage forms a taper from said insert end to said open end thereby forming an interference fit with the second end of said insert to close said passage when, the insert is fit within said adapter.

13. The adapter of claim 11 further comprising a shoulder in said passage intermediate said open end and said insert end so that when the second end of the insert is fit with said adapter, the second end substantially contacts said shoulder to close said passage.

14. The adapter of claim 13 wherein said shoulder is sized to form a substantially liquid tight seal around a perimeter of the porous membrane when said adapter is mounted on the cell culture insert.

15. The adapter of claim 11 wherein said open end of said insert comprises a surface substantially perpendicular to said axis, said surface having a plurality of spacers thereon.

16. The adapter of claim 15 wherein said spacers comprise hemispherical protuberances projecting from said surface, said spacers being suitable for supporting a cover above said second receptacle.

17. A method for forming a receptacle for containing fluid on an exterior side of a porous membrane of a cell culture insert comprising:

placing an adapter on a cell culture insert, said adapter consisting essentially of an insert end and an open end and having a passage with a longitudinal axis therethrough, said adapter having a shoulder intermediate said open end and said insert end, said insert end having an inside diameter sized to accept an end of the cell culture insert having a porous membrane with an interior side and an exterior second side mounted thereon, fitting the end of the insert into said adapter, thereby closing said passage, contacting said shoulder and forming a receptacle over said exterior side of said membrane open toward said open of said adapter.

18. A method for culturing one population of cells on one side of a porous membrane associated with a cell culture insert and another population of cells on another side of the porous membrane comprising:

mounting an adapter on a cell culture insert on an exterior side of a porous membrane of the cell culture insert having a first receptacle therewithin on a interior side of the membrane, said adapter consisting essentially of an insert end, a open end, having a passage with a longitudinal axis therethrough and having a shoulder intermediate said open end and said insert end, said insert end having an inside diameter sized to accept an end of the cell culture insert having the porous membrane mounted therein, so that when said adapter is releasably coaxially mounted over said end of the cell culture insert, the insert contacts said shoulder and closes said passage, thereby forming a second receptacle for containing fluid over the exterior side of the porous membrane open toward said open end of said adapter;

positioning the insert having said adapter mounted thereon on a surface so that said second receptacle is upward and open;

adding a suspension of a first population of cells in a suitable medium into said second receptacle;

incubating the insert so that said first population of cells forms a substantially confluent layer on the exterior side of said membrane;

removing the medium from said second receptacle;

removing said adapter from the insert;

placing the insert in a container so that the insert is suspended with said first receptacle upward and open;

adding a suspension of a second population of cells in a suitable medium into the first receptacle and onto the interior side of the membrane;

adding a suitable medium into the container; and incubating the container with the insert so that said second population of cells forms a substantially continuous layer on the interior side of the membrane.

* * * * *